United States Patent [19]
Merrell

[11] 4,282,759
[45] Aug. 11, 1981

[54] METHOD AND APPARATUS FOR NON-DESTRUCTIVE TESTING OF BEAM-LEAD INTEGRATED CIRCUIT CONNECTIONS

[75] Inventor: Jimmy D. Merrell, Madison, Ala.

[73] Assignee: The United States of America as represented by the Secretary of the Army, Washington, D.C.

[21] Appl. No.: 106,983

[22] Filed: Dec. 26, 1979

[51] Int. Cl.³ ............................................. G01N 3/08
[52] U.S. Cl. ...................................... 73/827; 228/104
[58] Field of Search ................. 73/827, 834, 826, 828, 73/830; 228/103, 104, 56.5

[56] References Cited

U.S. PATENT DOCUMENTS

| 3,634,930 | 1/1972 | Cranston | 73/827 X |
| 3,945,248 | 3/1976 | West | 73/827 |

Primary Examiner—Jerry W. Myracle
Attorney, Agent, or Firm—Nathan Edelberg; Robert P. Gibson; James T. Deaton

[57] ABSTRACT

A method and apparatus for non-destructive testing of beam-lead integrated circuit connections in which each of the leads from a chip beam-lead device has a pull tab made interval therewith with a weakened area and means for connecting a pull tool thereto to test the bond strength between the individual lead and the conductor to which the lead is bonded to determine if a predetermined bond exist between the lead and the conductor.

2 Claims, 4 Drawing Figures

METHOD AND APPARATUS FOR NON-DESTRUCTIVE TESTING OF BEAM-LEAD INTEGRATED CIRCUIT CONNECTIONS

DEDICATORY CLAUSE

The invention described herein may be manufactured, used, and licensed by or for the Government for governmental purposes without the payment to me of any royalties thereon.

BACKGROUND OF THE INVENTION

The presently known technology involving the testing of beam-lead devices deals with destructive testing such as the "Push-Off" testing of the entire bonding of the multiplicity of leads at one time or by other destructive methods. The "Push-Off" technology involves the use of a special substrate arranged such that a hole is directly under the bonded beam-lead device in order to allow the "Push-Off" test to be accomplished. When the bonded beam-lead device is desired to be tested with the prior art method, the force required to separate the bonded beam-leads of the device from the conductor pattern is recorded and the recorded force is then divided by the number of beam-leads of the bonded beam-leaded device to determine the calculated bond strength of each beam-lead. Other test methods involve destruction of the leads and/or other structure of the beam-lead device. As can be seen, these methods are not always accurate and further they require that the equipment be destroyed in making the test. Therefore, there is a need for a method of testing beam-leads without destroying the leads and the circuit in which they are connected.

Therefore, it is an object of this invention to provide a non-destructive test method for testing the bond strength of individual beam-leads to their respective conductor without destroying the bonding connection.

Another object of this invention is to provide a test structure that allows one to make a non-destructive test of the beam-lead of a beam-lead device.

A further object of this invention is to provide a beam-lead device in which the leads have a tab that can be pulled and broken to test the bond strength without breaking the bond between the conductor and its respective beam-lead.

Other objects and advantages of this invention will be obvious to those skilled in this art.

SUMMARY OF THE INVENTION

In accordance with this invention, a method and apparatus for non-destructive testing of beam-leaded devices is provided in which each individual lead of the beam-leaded device has a pull tab with a weakened area thereon in order to provide a non-destructive means for testing the beam-leads. The beam-lead device is tested by inserting a hook of a gram pull tester into an opening of the tab and pulling on the tab until the weakened area is broken. The weakened area is selected such that it will break when subjected to a predetermined pull and this predetermined amount being less than that required to break the tensil strength of the diffusion bond between the beam-leads and the conductors to which they are connected. In this manner, the bond strength of each individual beam-lead to its respective conductor is accurately tested in a non-destructive manner to determine the sufficiency of the bond strength of each individual lead.

DESCRIPTION OF THE PREFERRED EMBODIMENT

Figure 1:
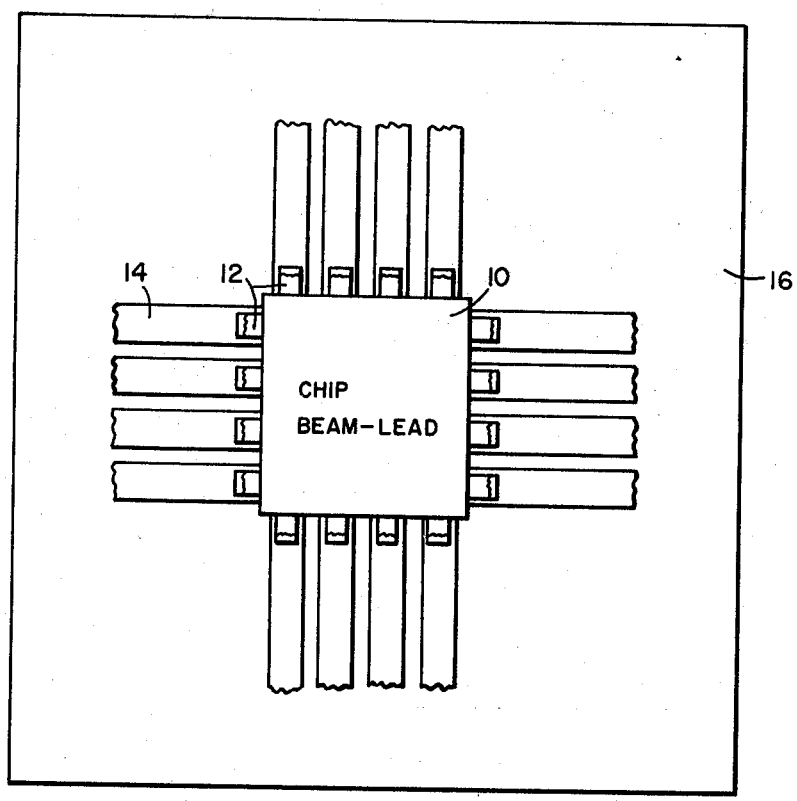
FIG. 1 is a top plan view of a typical beam-lead device on circuit with portions cut away.

Referring now to the drawing, in FIG. 1 a prior art device is illustrated and includes a chip beam-lead device 10 that is made of a ceramic material and has a multiplicity of circuits mounted therein and relative thereto. Chip beam-lead device 10 also has a plurality of gold beam-leads 12 leading therefrom with each beam-lead 12 being connected by diffusion bonding to a gold lead or conductor 14 mounted on substrate material 16. To illustrate the smallness of these devices, ten of the chip beam-lead devices 10 are connected to conductors on a one-inch square. That is, this invention is related to integrated circuit devices of very small dimension.

Figure 2:
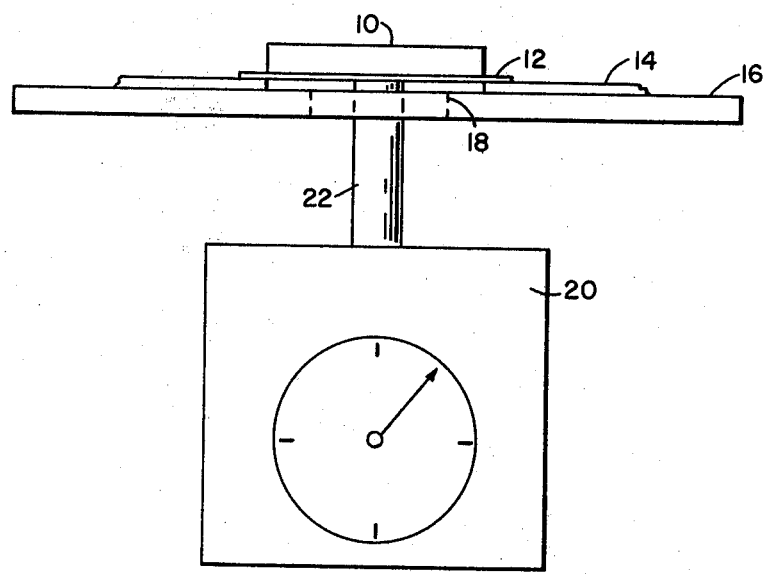
FIG. 2 is a schematic view of a test arrangement of a prior known testing method.

Referring now to FIG. 2, a prior art test arrangement is illustrated in which substrate 16 has an opening 18 therethrough and a gram push tester 20 has a shaft 22 positioned through opening 18 and onto a bottom surface of chip beam-lead device 10 to exert force thereon and test the bond strength of beam-leads 12 collectively. That is, gram push tester 20 has force applied through shaft 22 to chip beam-lead device 10 with all of beam-leads 12 connected to their respective conductors 14 to give an overall reading on gram push tester 12 of the force required to either break chip beam-lead device 10, or break beam-leads 12 or separate beam-leads 12 where they are bonded to conductors 14. As can be seen in this prior art arrangement, the actual bond strength of each beam-lead 12 to its respective conductor 14 can only be approximated since an average of the force required to perform the test can be asserted for each individual beam-lead. Further, this test obviously destroys the chip beam-lead device as well as the inner connecting structures. Therefore, test arrangements of this type are not as desirable as is needed.

Figure 3:
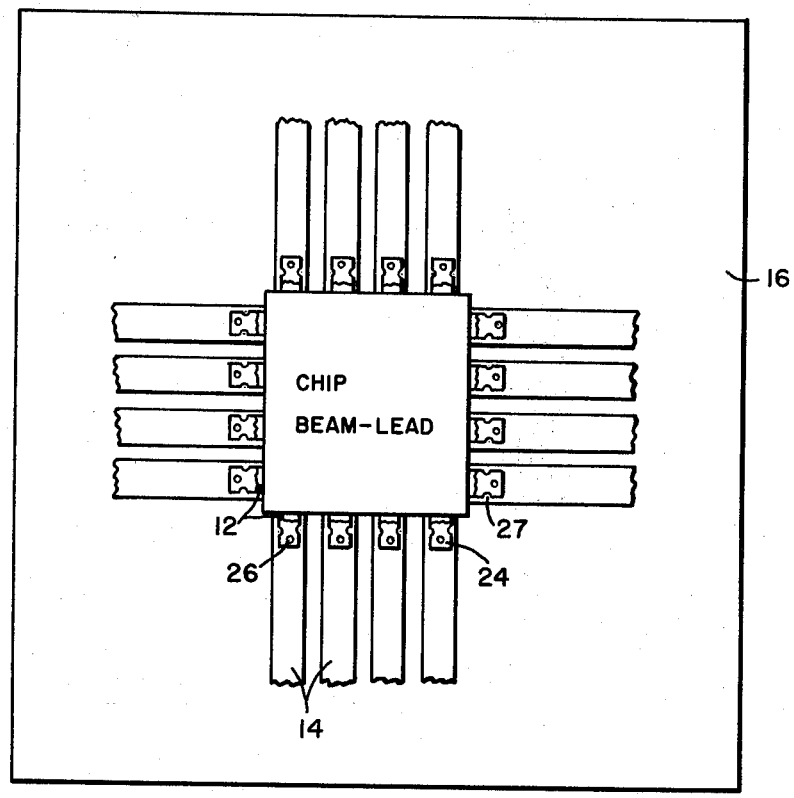
FIG. 3 is a top plan view of a beam-leaded device in accordance with this invention in which each of the beam-leads has a pull tab with a weakened area connecting the pull tab to the beam-lead proper.
Figure 4:
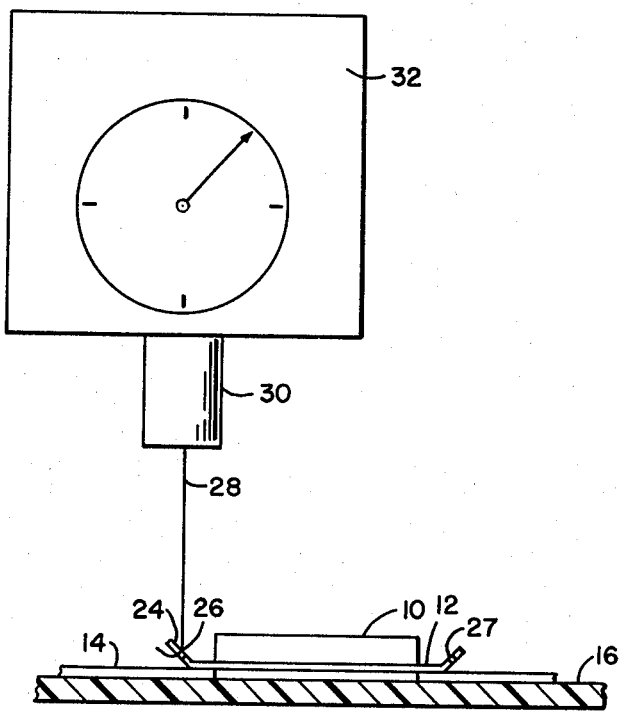
FIG. 4 is a side view illustrating a gram pull tester connected to the individual lead of one of the beam-leads of a ceramic chip.

Referring now to FIG. 3, a chip beam-lead device 10 of this invention is illustrated as having a plurality of gold beam-leads 12 each of which has a pull tab 24 with a hole 26 therethrough and a weakened area 27. Each tab 24 is designed to break at weakened area 27 when a predetermined pull force is exerted thereon. By providing each lead 12 with a pull tab, the diffusion bonding between each gold lead 12 and each gold conductor 14 can be accurately tested in a non-destructive manner. To carry out the pull test on each lead 12, a gram pull tester 32 is provided and has an inner connected shaft 30 and a hook 28 that is engaged in hole 26 of the desired beam-lead that is desired to be pulled to test the bond strength between the individual beam-lead and its conductor 14. Tab 24 will break at weakened area 27 and the test will be complete if the diffusion bonding is sufficient and the device will still be usable. That is, only if the diffusion bonding is insufficient will the device not be usable. Further, where the diffusion bonding is not sufficient, the device is not usable in this condition anyway. Therefore, nothing is actually lost in carrying out the testing of the leads as is made possible by this invention.

I claim:

1. A method for testing individual beam-leads of a chip beam-leaded device that has a multiplicity of beam-leads bonded to respective conductors that are mounted on a substrate and with each of said beam-leads having a pull tab with a weakened area, said method comprising connecting a pull hook of a pull tester to said pull tab by inserting said hook through an opening in said pull tab and then exerting a predetermined pull force from said pull tester to said pull tab until said pull tab is broken at said weakened area to determine that the individual beam-lead is sufficiently bonded to its respective conductor.

2. An integrated circuit device comprising a substrate material having a plurality of gold conductors on a surface thereof and a chip beam-lead device having a plurality of beam-leads with each of said beam-leads being connected to a respective one of said gold conductors by diffusion bonding, each said beam-lead having a tab end thereon that is spaced from said chip beam-lead device and from said diffusion bonding to allow said pull tab to be bent upward, each said beam-lead pull tab having a weakened area between a pulling end of said pull tab and said diffusion bonding between said beam-lead and said gold conductor, and said pull tab having an opening therethrough for insertion of a pulling device to test the bond strength between the respective beam-lead and the conductor to which it is bonded.

* * * * *